(12) United States Patent
Claus

(10) Patent No.: US 8,798,353 B2
(45) Date of Patent: Aug. 5, 2014

(54) APPARATUS AND METHOD FOR TWO-VIEW TOMOSYNTHESIS IMAGING

(75) Inventor: Bernhard Erich Hermann Claus, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 960 days.

(21) Appl. No.: 12/555,061

(22) Filed: Sep. 8, 2009

(65) Prior Publication Data
US 2011/0058724 A1    Mar. 10, 2011

(51) Int. Cl.
*A61B 6/03*    (2006.01)
*A61B 6/02*    (2006.01)

(52) U.S. Cl.
CPC .................................... *A61B 6/025* (2013.01); *G06T 2211/436* (2013.01)
USPC ............................................. 382/132; 378/37

(58) Field of Classification Search
CPC ........ A61B 6/502; A61B 6/025; A61B 6/466; A61B 6/4028; A61B 6/463; A61B 6/02; A61B 6/022; A61B 8/0825; A61B 8/463; A61B 6/461; G06T 2211/436; G06T 2207/30068; G06T 2207/10112; G06T 11/008; G06T 2200/24; G06T 2207/10012; G06T 11/006; H04N 13/0275; H04N 13/0011; H04N 13/0055; H04N 13/0059; H04N 13/0285; H04N 13/0452
USPC ................................ 378/4–29; 382/128–132
See application file for complete search history.

(56) References Cited

U.S. PATENT DOCUMENTS

| | | | |
|---|---|---|---|
| 6,553,356 B1 | 4/2003 | Good et al. | |
| 7,110,490 B2 | 9/2006 | Eberhard et al. | |
| 7,519,212 B2 | 4/2009 | Brady et al. | |
| 2001/0038681 A1* | 11/2001 | Stanton et al. | 378/55 |
| 2003/0194049 A1* | 10/2003 | Claus et al. | 378/22 |
| 2004/0101095 A1* | 5/2004 | Jing et al. | 378/37 |
| 2005/0113681 A1* | 5/2005 | DeFreitas et al. | 600/426 |
| 2005/0226375 A1* | 10/2005 | Eberhard et al. | 378/62 |
| 2006/0098855 A1* | 5/2006 | Gkanatsios et al. | 382/128 |
| 2006/0204076 A1* | 9/2006 | Avinash et al. | 382/154 |
| 2007/0036265 A1* | 2/2007 | Jing et al. | 378/37 |
| 2007/0092059 A1* | 4/2007 | Wayne Eberhard et al. | 378/37 |

(Continued)

OTHER PUBLICATIONS

Yoo et al., Dosimetric Feasibility of Cone-beam Ct-based treatment Planning Compared to Ct-based Treatment Planning, 2006, International Journal of Radiation Oncology Biology Physics, vol. 66, No. 5, pp. 1553-1561.*

(Continued)

*Primary Examiner* — Toan Ton
*Assistant Examiner* — John Corbett
(74) *Attorney, Agent, or Firm* — The Small Patent Law Group; Dean D. Small

(57) ABSTRACT

The invention is a directed to an apparatus for tomosynthesis imaging, wherein the apparatus comprises an x-ray source configured to irradiate an object with a beam of x-rays and a detector configured to detect the x-ray beam that passes through the object. The apparatus further comprises a computer programmed to perform a scan, wherein the scan comprises a translation of at least one of the x-ray source and the detector along a path, an acquisition of a tomosynthesis image dataset, and a reconstruction of one or more three-dimensional (3D) volumes adapted to one or more predetermined view directions, wherein at least one of the one or more predetermined view directions is aligned outside of a central view direction.

24 Claims, 5 Drawing Sheets

(56) References Cited

U.S. PATENT DOCUMENTS

| | | | |
|---|---|---|---|
| 2007/0268999 A1 | 11/2007 | Ullberg et al. | |
| 2008/0019581 A1* | 1/2008 | Gkanatsios et al. | 382/131 |
| 2008/0187095 A1* | 8/2008 | Boone et al. | 378/37 |
| 2008/0230074 A1* | 9/2008 | Zheng et al. | 128/869 |
| 2008/0247505 A1 | 10/2008 | Patnaik et al. | |
| 2009/0147073 A1* | 6/2009 | Getty | 348/51 |
| 2009/0216794 A1* | 8/2009 | Saptharishi | 707/102 |

OTHER PUBLICATIONS

Badea et al., Image Quality in Extended Arc Filtered Digital Tomosynthesis, 2001, Acta Radiologica, vol. 42, pp. 244-248.*

Pang et al., Just-in-time tomography (JiTT): a new concept for image-guided radiation therapy, 2005, Physics in Medicine and Biology, vol. 50, pp. N323-N330.*

Zhang et al., a Study of Megavoltage Beam Tomosynthesis, 2006, Medical Physics, vol. 33, No. 6, Abstract No. SU-FF-I-19, p. 2001.*

Kalender et al., Dose reduction in CT by on-line tube current control: principles and validation on phantoms and cadavers, 1999, European Radiology, vol. 9, pp. 323-328.*

Zhang et al., Comparing Digital Tomosynthesis to Cone-beam CT for Position Verification in Patients Undergoing Partial Breast Irradiation, Mar. 1, 2009, International Journal of Radiation Oncology Biology Physics, vol. 73, No. 3, pp. 952-957.*

Godfrey et al., Digital Tomosynthesis for Verification of Radiation Therapy Positioning: Preliminary Results From a Kilovoltage Onboard Imaging System, 2005, Medical Physics, vol. 32, No. 6, Abstract No. SU-FF-J-57, p. 1932.*

Goodsitt et al., The effects of stereo shift angle, geometric magnification and display zoom on depth measurements in digital Stereomammography, 2002, Medical Physics, vol. 29, No. 11, pp. 2725-2734.*

Cherniy et al., Use of Stereoscopic Vision for Analysis of Digital X-ray Images of Lungs, 2007, Biomedical Engineering, vol. 41, No. 5, pp. 214-217.*

Rafferty et al., Breast Tomosynthesis: One View or Two?, 2006, Radiological Society of North America 2006 Conference "RSNA2006", Abstract No. SSG01-04.*

* cited by examiner

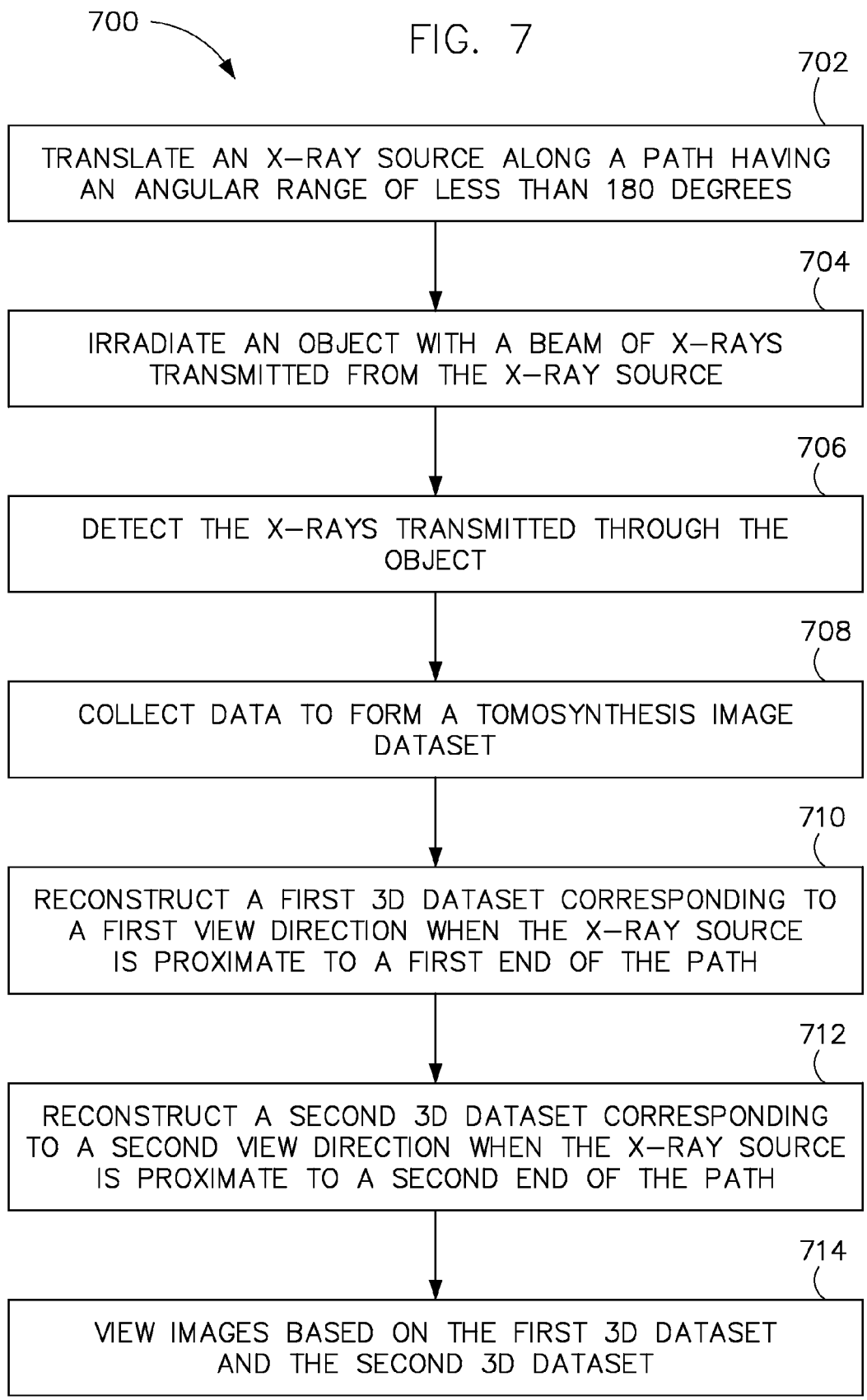

APPARATUS AND METHOD FOR TWO-VIEW TOMOSYNTHESIS IMAGING

BACKGROUND OF THE INVENTION

Embodiments of the invention relate generally to diagnostic imaging and, more particularly, to an apparatus and method for tomosynthesis imaging. The apparatus and method of the invention is capable of increasing patient throughput, increasing patient comfort, and decreasing radiation dose through the use of a single wide-angle tomosynthesis scan.

A widely used imaging tool for the early detection of breast cancer is x-ray mammography. In conventional x-ray mammographic imaging, a breast is immobilized and imaged in two different positions, thereby acquiring two separate projection images (views). The two views are known as craniocaudal (CC) and mediolateral oblique (MLO) projections. A CC projection is taken from above the patient, while an MLO projection is taken from an oblique side angle. FIGS. 1 and 2 illustrate a conventional CC projection 100 and MLO projection 200, respectively. As FIG. 1 shows, a patient's breast 102 is immobilized and compressed between a compression paddle 104 and a platform 106, shown in a horizontal orientation (i.e., generally perpendicular to the long patient axis). Below platform 106 is a detector 108, which receives x-ray beams emitted from an x-ray source 110. Similarly, the MLO projection 200 illustrated in FIG. 2 shows that a patient's breast 102 is immobilized and compressed between a compression paddle 104 and a platform 106, albeit at an angle different than that of the CC projection 100 with respect to the long patient axis. Again, a detector 108 is located below platform 106 with respect to the projection direction to receive x-ray beams emitted from an x-ray source 110.

Mammographic images based on the CC and MLO projection views are interpreted by trained clinicians to detect and identify potentially cancerous lesions in breast or other tissue. Unfortunately, images based on conventional projection views lack sensitivity and can be difficult to read due to the fact that superimposed tissue may mimic a lesion, or a lesion may be hidden by superimposed structure. Acquiring both a CC view and an MLO view partially addresses this issue, and thus the likelihood of detecting a lesion (or lesions) is increased. However, one still observes a high rate of false negative and/or false positive results. Furthermore, each of the CC and MLO projection views require separate breast compressions, leading to increased radiation dose, increased patient discomfort and reduced patient throughput.

In an effort to address the inadequacies of conventional mammographic imaging using separate CC and MLO projection views, a mammographic technique known as three-dimensional tomosynthesis imaging was developed. Tomosynthesis imaging was found to help in resolving the ambiguities associated with overlapping tissue mimicking a lesion or overlying tissue hiding a lesion, two major causes of false positives and false negatives in conventional mammographic imaging techniques. As FIG. 3 illustrates, a three-dimensional tomosynthesis scan 300 involves the movement of an x-ray source 310 in an arced or linear path at a predefined angle about a patient's breast 302, with patient's breast 302 again immobilized and compressed between a compression paddle 304 and a platform 306. A detector 308 is located below platform 306, where detector 308 receives x-ray beams emitted from x-ray source 310. Typical three-dimensional tomosynthesis imaging uses a stationary flat-panel x-ray detector and acquires a set of projection images (i.e., the tomosynthesis image dataset) in a step-and-shoot mode (i.e., the x-ray source moves between exposures, and a new exposure is taken at each new x-ray source position along the path). Projection angles of the x-ray source 310, which correspond to the positions of x-ray source 310 at which projection images are acquired, are arranged in a 1D or 2D path, which is generally symmetrical around the z-axis, i.e., the axis orthogonal to the x-ray detector plane. From the tomosynthesis image dataset a volumetric 3D dataset is reconstructed in a coordinate system where the x/y plane corresponds to the detector plane, and the z-axis is the axis orthogonal to the detector plane. The reconstructed volume is generally arranged as a set of x/y slices 312 for different z-values (or heights above the detector), wherein the slices are arranged parallel to the x-ray detector plane.

Viewing of the reconstructed volume in conventional tomosynthesis is generally performed in a slice-by-slice mode (e.g., in a cine-loop). Other viewing modes (e.g., thick slices, volume rendering, etc.) are used as well. It is important to note that slice-by-slice viewing of the 3D volume reconstructed in the x/y/z coordinate system implies a view direction 314 of the reconstructed volume in the z-axis direction. Also, the reconstruction algorithms in conventional tomosynthesis imaging are implicitly optimized for the conventional viewing techniques, and thereby discard some image information that is present in the tomosynthesis image dataset, which degrades the perceived image quality for the implicitly chosen viewing direction. Using novel approaches, such as those discussed herein, the image information from the tomosynthesis image dataset may be fully used.

While three-dimensional tomosynthesis allows significant improvements in detection and recall rate, a single tomosynthesis acquisition sequence at a small acquisition angle (e.g., ±15 degrees), such as that shown in FIG. 3, is insufficient for ideal three-dimensional imaging. Thus, conventional tomosynthesis imaging techniques incorporate a second tomosynthesis acquisition sequence, such as tomosynthesis scan 400 shown in FIG. 4, into the imaging procedure. By acquiring images using tomosynthesis imaging from two views (i.e., those shown in FIGS. 3 and 4, corresponding to the conventional CC and MLO views), benefits similar to those found in conventional mammographic imaging using separate CC and MLO projection views can be achieved, while each individual tomosynthesis dataset exhibits better clinical performance than its single-image counterpart. However, the relatively small angular range scan in each of the two tomosynthesis acquisitions is not sufficient to produce an image dataset having good three-dimensional resolution. Additionally, by acquiring images via two acquisitions, two separate breast compressions are again needed, thereby adding to patient discomfort, radiation dosage, and scan time. The breast compressions also limit the benefits of three-dimensional tomosynthesis imaging, as the breast is essentially compressed into a flat configuration.

Therefore, it would be desirable to design an apparatus and method of wide angle, multi-view mammographic tomosynthesis imaging without the need for breast repositioning or multiple breast compressions, which fully utilizes the collected information contained in the tomosynthesis image dataset.

BRIEF DESCRIPTION OF THE INVENTION

The invention is a directed to an apparatus for tomosynthesis imaging, wherein the apparatus comprises an x-ray source configured to irradiate an object with a beam of x-rays and a detector configured to detect the x-ray beam that passes through the object. The apparatus further comprises a computer programmed to perform a scan, wherein the scan comprises a translation of at least one of the x-ray source and the detector along a path, an acquisition of a tomosynthesis image dataset, and a reconstruction of one or more three-dimensional (3D) volumes adapted to one or more predetermined view directions, wherein at least one of the one or more predetermined view directions is aligned outside of a central view direction.

Another aspect of the invention is directed to a method of forming three-dimensional images of an object, wherein the method comprises irradiating an object with a beam of x-rays at a plurality of positions along a path, wherein the beam of x-rays is emitted from an x-ray source, and acquiring a tomosynthesis image dataset based on x-rays detected by an x-ray detector. The method further comprises reconstructing one or more three-dimensional (3D) volumes from the tomosynthesis image dataset, wherein the reconstructing of the one or more 3D volumes is adapted to one or more predetermined view directions, and wherein at least one of the one or more predetermined view directions is aligned outside of a central view direction.

According to another aspect to the invention, a tomosynthesis imaging system for forming three-dimensional images of an object is shown, the system comprising an x-ray source configured to irradiate an object with x-rays and an x-ray detector positioned relative to the x-ray source to detect x-rays transmitted by the x-ray source. The system also comprises a computer programmed to translate one of the x-ray source and the x-ray detector during a scan such that one of the x-ray source and the x-ray detector travels along a path with respect to an object to be imaged, and acquire a tomosynthesis image dataset. The computer is also programmed to reconstruct one or more three-dimensional (3D) volumes from the acquired tomosynthesis image dataset, wherein the one or more 3D volumes correspond to one or more predetermined view directions, and wherein at least one of the one or more predetermined view directions is oriented outside of a central view direction.

Various other features and advantages will be made apparent from the following detailed description and the drawings.

BRIEF DESCRIPTION OF THE DRAWINGS

The drawings illustrate one preferred embodiment presently contemplated for carrying out the invention.

In the drawings:

FIG. 7 illustrates a flowchart detailing an embodiment of the invention.

DETAILED DESCRIPTION

A system and method of tomosynthesis imaging are shown that are capable of increasing patient throughput, increasing patient comfort, and decreasing radiation dose through the use of a single wide-angle tomosynthesis scan. The wide-angle tomosynthesis scan can be used to generate two or more separate three-dimensional (3D) datasets, wherein each 3D dataset corresponds to a preferred view direction with respect to the object being scanned. Each of the datasets may be viewed according to methods known in the art (e.g., slice-by-slice viewing, volume rendering, etc.), or using methods described herein below.

Figure 5:
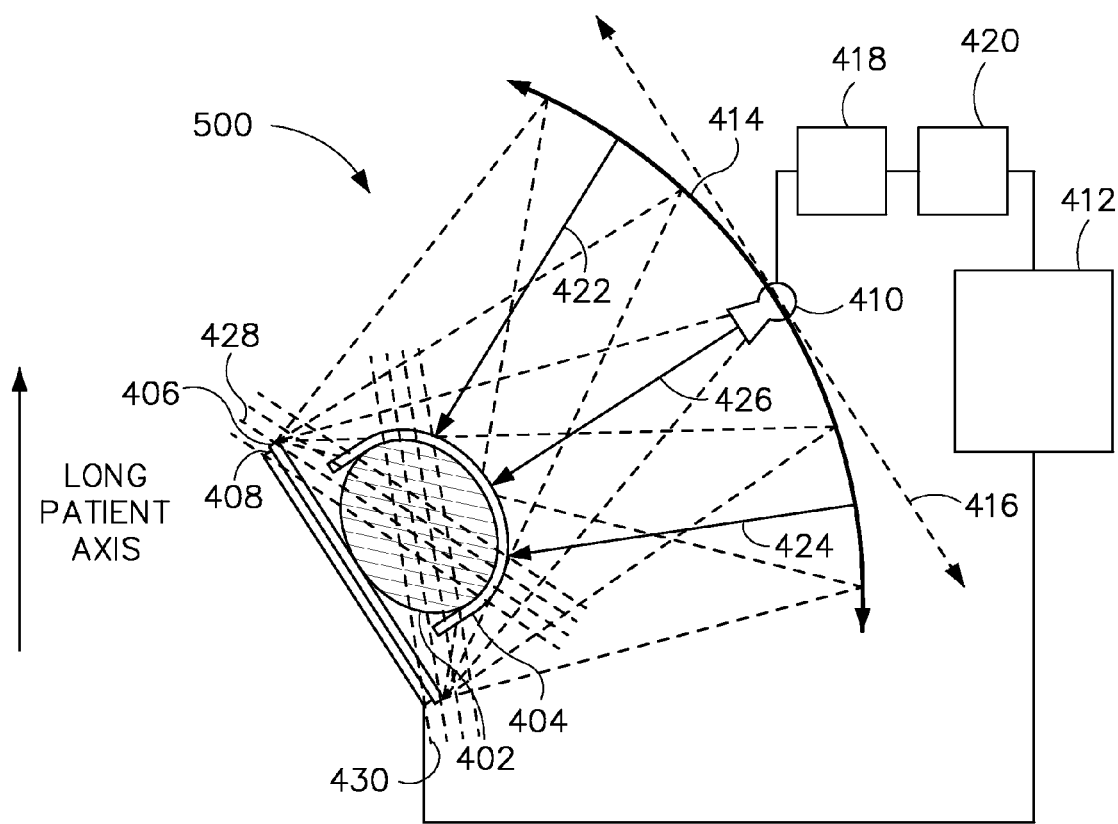
FIG. 5 illustrates a wide angle three-dimensional tomosynthesis scan and resulting reconstructed 3D volumes according to an embodiment of the invention.

Referring to FIG. 5, a wide-angle tomosynthesis imaging device 500 according to an embodiment of the invention is shown. Wide-angle tomosynthesis imaging device 500 incorporates the movement of an x-ray source 410 in an arced path 414 at a predefined angle about a patient's breast or other object 402. The breast or object 402 may be immobilized between a compression paddle 404 and a platform 406.

FIG. 5 also shows a detector 408 located adjacently to platform 406. Detector 408 is configured to receive x-ray beams emitted from x-ray source 410 as x-ray source 410 follows arced path 414 about breast or object 402. A computer 412 is operably connected to both detector 408 and x-ray source 410. In this way, data acquired by detector 408 can be processed by computer 412 to produce an image to be displayed, and computer 412 can also be programmed to control the translation of x-ray source 410 along path 414. Computer 412 is also coupled to an x-ray source support 418 and a motor controller 420. The translation of x-ray source 410 via x-ray source support 418 is controlled by commands sent to motor controller 420 from computer 412. Computer 412 also controls timing of x-ray source activation, detector readout, and x-ray source motion. The total angular range of arced path 414 may vary, but is limited by the total angular range allowed by x-ray source support 418. For the purposes of mammography, that total possible angular range of x-ray source support 418 is understood to be an angle of 180 degrees or less. The larger the angular range, the better the 3D resolution. For the purposes of the invention, and for the purposes of tomosynthesis imaging, a 60-120 degree total angular range provides generally good 3D resolution.

X-ray source 410 is translated via x-ray source support 418 along arced path 414 during a single scan, wherein the scan encompasses the region from a beginning point of the total angular range of the scan to an endpoint of the total angular range of the scan. As discussed above, the total angular range may be 60-120 degrees, but is not limited as such, and may be larger or smaller. As the scan commences, x-ray source 410 emits x-ray beams at predetermined positions along the arcuate path such that a plurality of x-ray projection images of breast or object 402 are acquired. One or more 3D volumetric datasets are then reconstructed from the tomosynthesis image dataset, where each reconstruction may be adapted to a specific view direction. With embodiments of the invention, it is preferable to have two or more view directions, such as view directions 422 and 424 shown in FIG. 5, with at least one of view directions 422, 424 being distinct from a view direction 426 along the z-axis (i.e., the axis directly orthogonal to the detector plane, or the central projection direction). In one embodiment, the x-ray source angles for the acquisition are clustered around the chosen view directions 422, 424, with fewer or possibly no projections at projection angles located away from view directions 422, 424. Preferably, view directions 422, 424 are separated by 30-90 degrees. In one embodiment, desired view directions 422, 424 are chosen to be near the extreme ends of the angular range of the scan, and therefore a greater number of projections are to be clustered at the extreme ends of the angular range, with fewer or possibly no projections at the center region of the angular range. From the tomosynthesis image dataset comprising these clustered projections at the respective ends of the angular range, at least two 3D volumes corresponding to two distinct view directions 422, 424 can be reconstructed, each of these view directions 422, 424 being located away from central view direction 426. Central view direction 426 is associated with the z-axis, i.e., the axis orthogonal to the x-ray detector plane, which defines the center region of the angular range. The desired view directions 422, 424 may be, e.g., 30 degrees apart, 45 degrees apart, or 60 degrees apart.

As an example, a 90 degree scan may use 9 views at 4 degree increments from −45 to −13 degrees, 3 more views at 0 and +/−6.5 degrees, and 9 additional views in 4 degree increments from 15 to 45 degrees, for a total of 21 projections. This scan configuration is adapted to reconstruct two separate 3D volumes for view directions at about +/−29 degrees. As another example, a 60 degree scan (from −30 to +30 degrees) may use fourteen total projections, wherein two separate subsets of seven projections are respectively clustered within 18 degree ranges at respective ends of the scan. In this way, two distinct 3D datasets, corresponding to two distinct view directions (e.g., at +/−21 degrees) can be computed from the respective subsets of projections at the extreme ends of the angular range. As such, the invention enables two 3D datasets corresponding to two distinct viewpoints to be reconstructed from a single tomosynthesis image dataset (that is, acquired using a single scan) without the need for repositioning, or re-immobilizing, breast or object 402, which thereby increases patient throughput, as no subsequent scans are needed, and decreases patient discomfort, as no subsequent breast (or object) compression is needed.

From the acquired tomosynthesis image dataset, two or more distinct 3D volumes may be reconstructed. These reconstructions are adapted to the chosen view directions. In one embodiment, the slice orientation in each of the reconstructions is perpendicular to the view direction. For example, as shown in FIG. 5, one 3D volume may consist of slices 428 that are arranged essentially perpendicular to the corresponding view direction 422, and another 3D volume may consist of slices 430 that are arranged essentially perpendicular to the corresponding view direction 424. The viewing of the two volumes may be performed using slice-by-slice viewing, thick slice viewing, volume rendering, etc.

While the above example describes a 60 degree tomosynthesis scan using fourteen total projections at the respective ends of the angular range of the scan, it is to be understood that the invention is not limited as such. For example, a greater or lesser number of projections can be used, and projections may also be completed at the central region of the angular scan. The view directions may be predetermined, may be determined through manual selection by a user, or using an automatic selection via a CAD-type evaluation step by computer 412. It is to be noted that more than two desired view directions may be chosen. In one embodiment, only a single view direction, distinct from the axis orthogonal to the detector plane, is determined. Furthermore, the imaging parameters of the scan may be adapted dependent upon the orientation of one or more of the given view directions. That is, imaging parameters such as projection angles, dose per angle, x-ray source speed during projection acquisition (in the case of a continuous scan system, as discussed further below), image resolution, and field-of-view may be altered depending on the desired view directions. Generally, the acquisition parameters are such that the projection images at x-ray source positions near the view directions are more closely spaced, and have better image quality (i.e., higher dose, less tube motion during exposure, etc.), than the projection images that are farther away from the view directions. For example, with two view directions near the respective extreme ends of the scan, the projections at the central region may be low-dose projections, the x-ray source speed may be higher and the image resolution lower at projection angles in the central region, and the projections in the central region may be spaced apart at greater angular intervals than those projections at the ends of the angular range of the scan corresponding to the desired view directions, as the projections at the central region are not as vital to the reconstruction of the 3D images at the desired end view directions. However, the projections may also be evenly distributed at equidistant intervals throughout the angular range to allow for more than two 3D images to be reconstructed, or in order to enable a post-acquisition selection of the view directions. It is also possible for the projections at the central region of such a scan to have a lower associated dose than those projections at the ends of the angular range of the scan, even if projections are completed at equidistant intervals. In this way, data from the central regions of the scan may be acquired, but patient dose is still minimized.

While FIG. 5 illustrates that x-ray source 410 is translated along arced path 414 with respect to breast or object 402 and detector 408, it is to be understood that x-ray source 410 may instead be translated along a linear path 416 with respect to both breast or object 402 and detector 408. A tomosynthesis scan following such a linear path 416 is also capable of acquiring tomosynthesis image datasets from which two or more 3D volumes corresponding to two or more desired view directions can be computed, and thus at least two 3D images from two viewpoints can be reconstructed using a single tomosynthesis scan having either an arced or a linear path. In other system configurations, the tomosynthesis image dataset may be acquired using a continuous (as opposed to a step-and-shoot) scan, where the speed of the x-ray source during the scan may be controlled in order to optimize image quality. Furthermore, it is to be noted that in one embodiment, only a reconstruction for a single view direction is contemplated, wherein the single view direction is away from the central projection direction.

Figure 1:
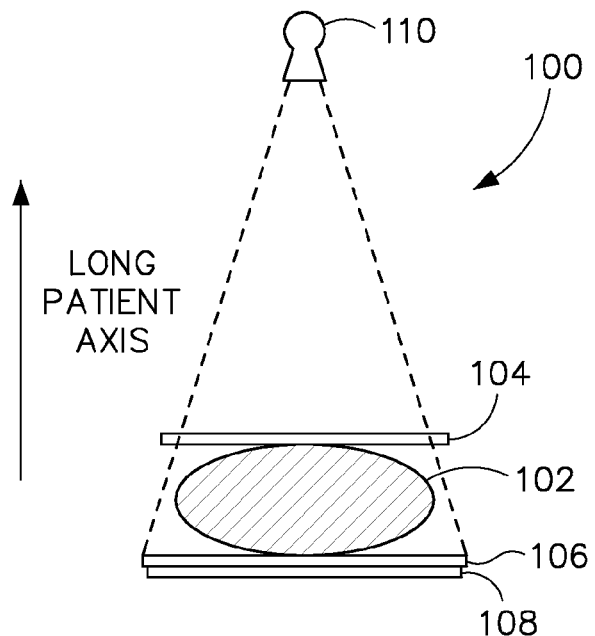
FIG. 1 illustrates a conventional cranio-caudal (CC) projection for mammographic imaging.
Figure 2:
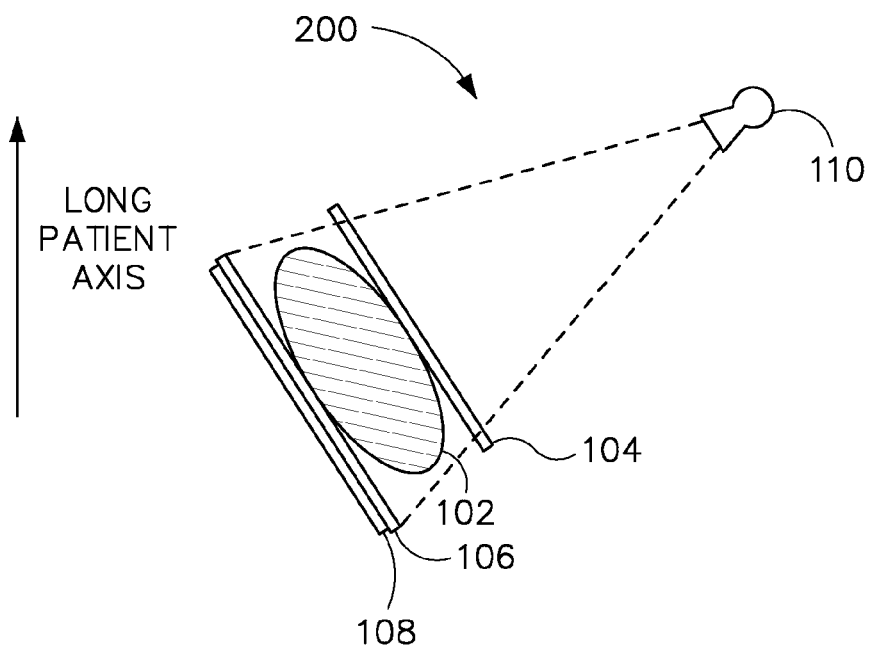
FIG. 2 illustrates a conventional mediolateral oblique (MLO) projection for mammographic imaging.
Figure 3:
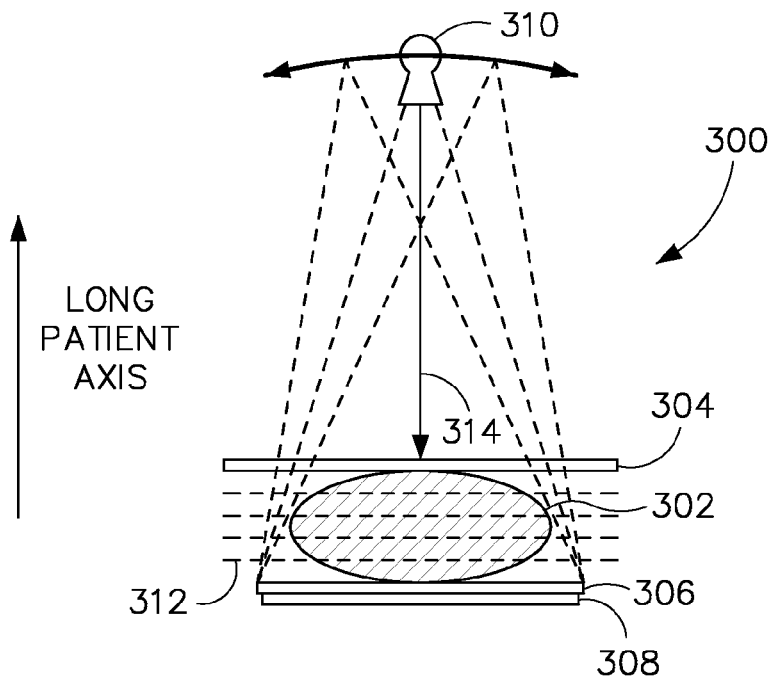
FIG. 3 illustrates a conventional three-dimensional tomosynthesis scan from a cranio-caudal (CC) view.
Figure 4:
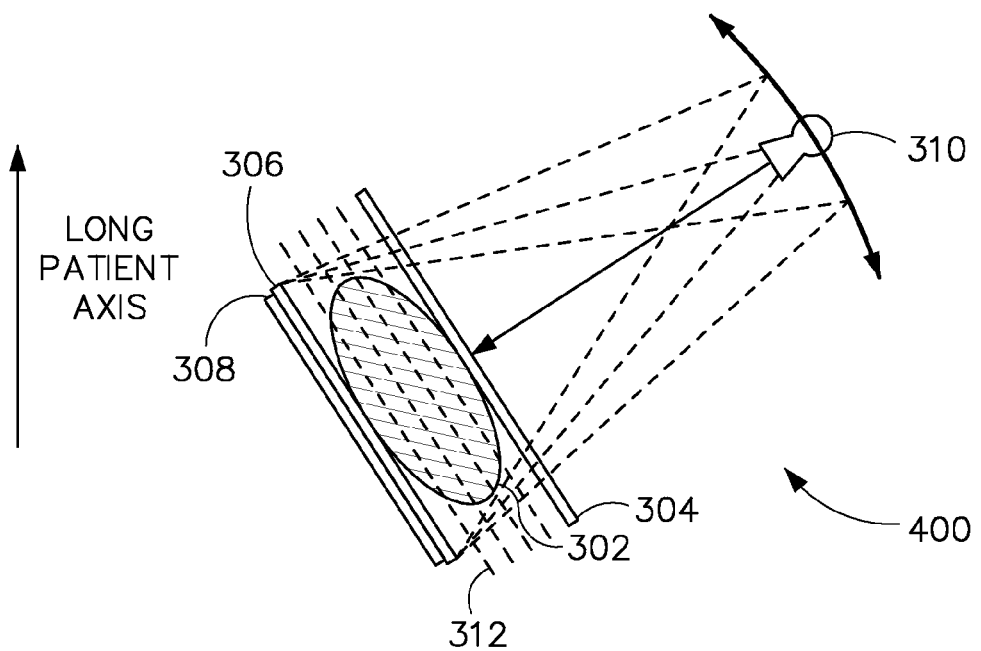
FIG. 4 illustrates a conventional three-dimensional tomosynthesis scan from a mediolateral oblique (MLO) view.

Upon acquisition of the tomosynthesis image datasets, two or more 3D images corresponding to the two or more desired view directions can be generated through separate reconstruction of the two or more 3D datasets. It is to be understood that the reconstruction of each 3D image may use all of the tomosynthesis image dataset, or a suitably chosen subset of the projection images that includes the projections that are closest to the respective view direction. The coordinate system used for reconstruction may also be adapted depending on the view direction of each respective view direction. For example, in FIG. 5, view directions 422 and 424 represent desired view directions. Two sets of slices 428 and 430 are orthogonally oriented with respect to view directions 422 and 424, respectively. Unlike slices 312 illustrated in FIG. 3, slices 428 and 430 are not oriented parallel to x-ray detector surface 408. That is, the slices that are reconstructed may be arranged substantially orthogonal relative to the respective view directions. It is to be noted that the reconstruction and viewing methods of the present invention may also be applied to regions of interest (ROIs), where the ROIs may be manually selected, or selected with the help of a CAD (computer aided detection) type processing step, e.g., based on a conventional tomosynthesis 3D volume. For such a ROI, reconstructions using various view directions and/or various slice orientations may be used, thereby allowing for optimal inspection of the imaged structures within the ROI.

Common reconstruction algorithms for tomosynthesis imaging include filtered backprojection (FBP), generalized filtered backprojection (GFPB), maximum likelihood (ML-EM), algebraic reconstruction technique (ART), direct algebraic reconstruction technique (DART), and matrix inversion tomosynthesis (MITS). These reconstruction algorithms are applicable with the invention. According to an embodiment of the invention, an optimized generalized filtered backprojection reconstruction (GFBP) is preferably used, wherein the generalized filtered backprojection algorithm is optimized for each specific view direction and/or slice orientation. Such optimization of the reconstruction algorithm allows for improved image quality and minimized image artifacts. In particular, using an optimized GFBP-type reconstruction algorithm, the (pre-processed) projection images are generally filtered with a ramp-type filter, where higher frequencies in the image are enhanced more than low frequency image content, before backprojecting and combining the different projection images. In an optimized GFBP-type reconstruction algorithm, the highest frequencies are more enhanced in projection images corresponding to projection angles that are close to the desired view direction than in projection images corresponding to projection angles that are farther away from the desired view direction. In another embodiment, the reconstruction for a given view direction uses only the images from the tomosynthesis image dataset that are associated with angles that are close to the desired view direction, while discarding projection images associated with projection angles far away from the desired view direction. Furthermore, any of the reconstruction techniques described herein may also be combined with artifact management techniques such as order statistics-based backprojection or weighted backprojection. Also, the described methods may be used in an iterative manner, by repeatedly updating the reconstructed 3D volume. Such artifact management techniques may be applied to all or to a selected subset of the reconstruction steps (e.g., different techniques may be applied at different iteration steps) to further optimize the reconstruction for each view direction.

Beyond the optimized reconstruction algorithm discussed above, additional embodiments for generating the 3D volumes at each respective preferred view direction are also contemplated as embodiments of the invention. For example, 3D volumes corresponding to two or more view directions may be generated through separate post-filtering steps applied to a single reconstructed 3D dataset. In each view direction (e.g., the view direction from the respective ends of the angular range of the scan), a different filter may be applied, thereby optimizing the image quality with respect to each view direction. Additionally, a multi-scale reconstruction scheme may be used. In such a reconstruction scheme, coarse scale information from every projection in the scan is used to reconstruct a coarse scale 3D representation of the imaged object (e.g., a breast). To create a 3D volume corresponding to a desired view direction, fine scale information from subsets of projections that are near the desired view direction are added to the coarse scale volume, thereby forming a 3D volume of an image from the view direction pertaining to a first view direction. Fine scale information from a separate subset of projections associated with projection angles close to the second view direction is then used for the reconstruction of a 3D volume corresponding to a second view direction. Variations of this multi-scale approach may also be used, such as using more than two scales and using varying number of projection images for each scale.

As an alternative to forming two separate 3D images from two 3D datasets at preferred view directions, a further embodiment of the invention enables two reconstructions from two or more 3D datasets to be merged. The local "sharpness", or detail resolution, at each location can be measured. Using the image information from the "sharper" reconstruction at each location, a merged reconstruction is capable of being generated. This merged 3D reconstruction combines the benefits of both optimized reconstructions at separate view directions.

Figure 6:
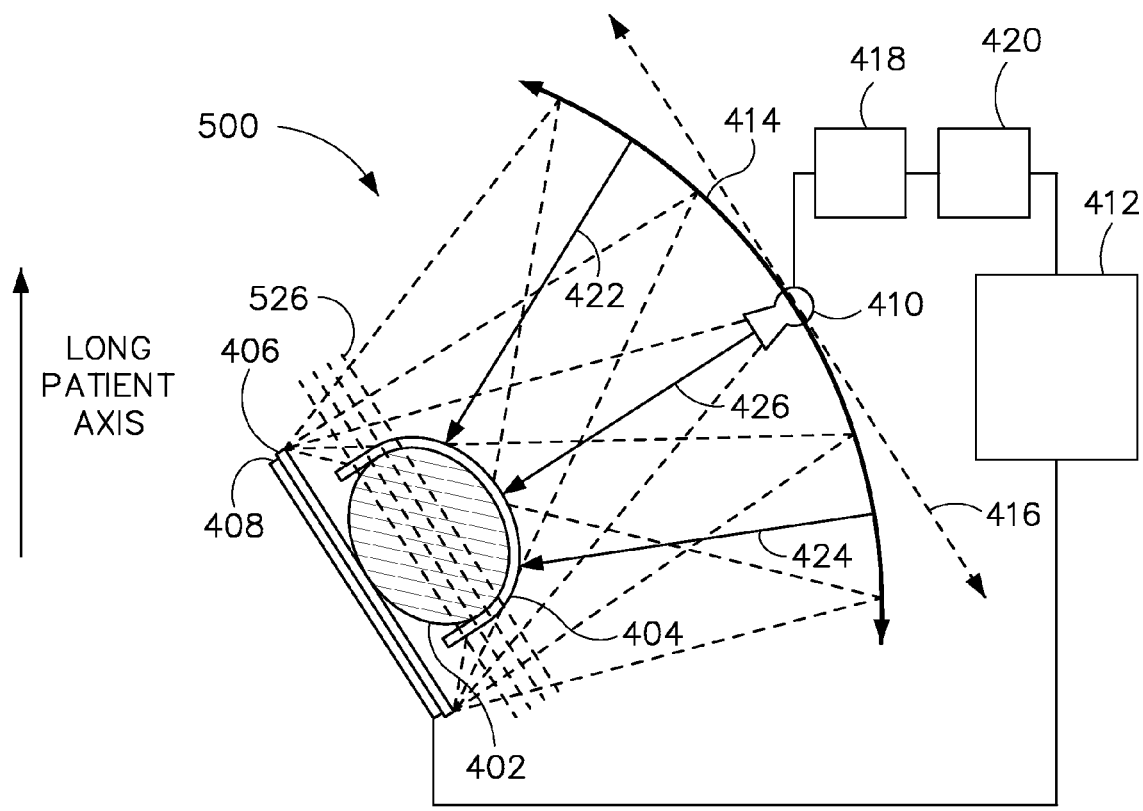
FIG. 6 illustrates a wide angle three-dimensional tomosynthesis scan and resulting reconstructed 3D volumes according to another embodiment of the invention.

After reconstruction of the 3D images is completed, the images may be viewed in a variety of configurations. For example, the reconstructed volumes may be viewed in a slice-by-slice mode or as a volume rendering. When viewed in a slice-by-slice mode, it may be advantageous to have the slice orientation for the two or more viewpoints aligned. Preferably, this slice orientation is already used in the 3D reconstruction step. For example, FIG. 6 illustrates an embodiment where the reconstructions of the two or more 3D volumes are performed such that the coordinate systems in both 3D volumes are aligned. For the reconstruction of a 3D volume for a given view direction, the slices (i.e., the coordinate system used in the 3D reconstruction) generally do not need to be aligned substantially perpendicular to the desired view direction. Slices 526 are oriented parallel to the plane of x-ray detector 408, as opposed to orthogonal to the desired view direction, as is illustrated in FIG. 5. Note that slices 526 in FIG. 6 represent the coordinate system used in the reconstruction of a respective 3D volume for any of view directions 422, 424, and 426. In this case, viewing the 3D volumes side-by-side may be advantageous, since now the two volumes can easily be registered, meaning that the same point locations within slices in the two volumes correspond to the same physical 3D location. That is, in each volume, the same point corresponds to the same physical location seen from different view directions, and viewing corresponding slices from the two (or more) 3D volumes shows the same physical plane through the imaged object, thereby facilitating image review and interpretation. However, the slices do not have to be aligned, and may be arranged perpendicular to the respective view direction, as is again shown in FIG. 5. In another embodiment, the selection of a point or region of interest in a slice of one 3D dataset may be used to update the display of the second dataset to the corresponding slice location, wherein the corresponding region of interest may be highlighted. Other viewing configurations, based on manual or automated selection of regions of interest (ROIs) in the respective datasets, may be considered as well. Thus, it is to be understood that embodiments of the invention enable a variety of configurations for viewing the reconstructed images.

In another aspect of the invention, FIGS. 5 and 6 both illustrate that the compression paddle 404 is not substantially planar, but is instead curved. Preferably, curved paddle 404 does not fully compress breast or object 402 so as to allow breast or object 402 to better retain its natural shape. While platform 406 is shown to be a flat surface, it is to be understood that platform 406 and/or detector 408 may also be curved to support breast or object 402. In this way, breast or object 402 is not fully compressed into a flat state, and thus the benefits of 3D imaging are able to be fully realized.

Referring now to FIG. 7, a flowchart 700 detailing an embodiment of the invention is shown. At block 702, an x-ray source is translated along a path having an angular range less than 180 degrees (e.g., 60 degrees). An object (e.g., a breast) is irradiated with a beam of x-rays transmitted from the x-ray source at block 704. At block 706, x-rays transmitted through the object are detected by an x-ray detector. Data is then collected to form a tomosynthesis image dataset at block 708.

Next, at block 710, a first 3D dataset is reconstructed corresponding to a view direction that is close to the projection direction when the x-ray source is proximate to a first end of the path of translation. At block 712, a second 3D dataset is reconstructed corresponding to a second view direction that is close to the projection direction when the x-ray source is proximate to the second end of the path opposite the first end. Finally, at block 714, images based on each of the first and second 3D datasets are viewed.

While the embodiments of the invention detailed above comprised an x-ray source capable of translation along an arced or linear path, the invention is not limited as such. For example, alternative embodiments of the invention may include distributed x-ray source points, either alone or in combination with x-ray source motion. Furthermore, the x-ray detector may be either a stationary or a moving x-ray detector, and the x-ray detector may be planar, curved or one-dimensional. Projections may also be collected by scanning a linear detector array, or by scanning both an x-ray detector and an x-ray source. Other scanning configurations, such as moving the object to be scanned past a stationary x-ray source in combination with appropriate detector configurations (e.g., as used in systems for luggage scanning) are also possible with this invention. In one embodiment, the imaging process comprises dual- or multi-energy imaging. In another embodiment, a contrast medium (e.g., iodine) may be administered at the time of imaging.

Additionally, while mammographic tomosynthesis imaging is an ideal application of the present invention, there are also other possible applications unrelated to mammography in which two-view tomosynthesis imaging may be useful. Examples of such applications include chest and other medical imaging, as well as security and non-destructive evaluation (NDE) applications. Furthermore, systems other than mammographic imaging systems may be used to acquire tomosynthesis sequences according to the present invention, e.g., chest tomosynthesis systems, C-arm systems, etc.

In view of the above, embodiments of the invention disclosed herein are shown to be capable of increasing patient throughput, increasing patient comfort, and decreasing radiation dose during a tomosynthesis imaging scan, while obtaining optimized 3D reconstructed images from at least two viewpoints from a single tomosynthesis scan.

A technical contribution for the disclosed method and apparatus is that it provides for a computer implemented to perform wide-angle tomosynthesis imaging in accordance with the embodiments described herein.

Thus, the invention is directed to an apparatus for tomosynthesis imaging, wherein the apparatus comprises an x-ray source configured to irradiate an object with a beam of x-rays and a detector configured to detect the x-ray beam that passes through the object. The apparatus further comprises a computer programmed to perform a scan, wherein the scan comprises a translation of at least one of the x-ray source and the detector along a path, an acquisition of a tomosynthesis image dataset, and a reconstruction of one or more three-dimensional (3D) volumes adapted to one or more predetermined view directions, wherein at least one of the one or more predetermined view directions is aligned outside of a central view direction.

Another aspect of the invention is directed to a method of forming three-dimensional images of an object, wherein the method comprises irradiating an object with a beam of x-rays at a plurality of positions along a path, wherein the beam of x-rays is emitted from an x-ray source, and acquiring a tomosynthesis image dataset based on x-rays detected by an x-ray detector. The method further comprises reconstructing one or more three-dimensional (3D) volumes from the tomosynthesis image dataset, wherein the reconstructing of the one or more 3D volumes is adapted to one or more predetermined view directions, and wherein at least one of the one or more predetermined view directions is aligned outside of a central view direction.

According to another aspect to the invention, a tomosynthesis imaging system for forming three-dimensional images of an object is shown, the system comprising an x-ray source configured to irradiate an object with x-rays and an x-ray detector positioned relative to the x-ray source to detect x-rays transmitted by the x-ray source. The system also comprises a computer programmed to translate one of the x-ray source and the x-ray detector during a scan such that one of the x-ray source and the x-ray detector travels along a path with respect to an object to be imaged, and acquire a tomosynthesis image dataset. The computer is also programmed to reconstruct one or more three-dimensional (3D) volumes from the acquired tomosynthesis image dataset, wherein the one or more 3D volumes correspond to one or more predetermined view directions, and wherein at least one of the one or more predetermined view directions is oriented outside of a central view direction.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An apparatus for tomosynthesis imaging comprising:
    an x-ray source configured to irradiate an object with a beam of x-rays;
    a detector configured to detect the x-ray beam that passes through the object; and
    a computer programmed to:
        perform a single scan, the single scan comprising:
            a translation of at least one of the x-ray source and the detector along a path during the single scan;
            an acquisition of a tomosynthesis image dataset during the single scan; and
            a reconstruction of two or more three-dimensional (3D) volumes respectively adapted to two or more predetermined view directions from the tomosynthesis image dataset, wherein at least one of the two or more predetermined view directions is aligned outside of a central view, the at least one predetermined view direction corresponding to a location of the x-ray source different than a location of the x-ray source corresponding to the central view, the at least one redetermined view direction being non-orthogonal to an x-ray detector plane of the detector and distinct from a view direction of the central view.

2. The apparatus of claim 1 wherein imaging parameters of the single scan are adapted based on an orientation of the two or more predetermined view directions.

3. The apparatus of claim 2 wherein the imaging parameters comprise at least one of projection angles, dose-per-angle, x-ray source speed during acquisition, image resolution, and field-of-view.

4. The apparatus of claim 1 wherein two of the two or more predetermined view directions are proximate ends of the path such that the predetermined view directions are closer to the ends than a view direction of the central view.

5. The apparatus of claim 4 wherein the two of the two or more predetermined view directions are separated by one of 30 degrees, 45 degrees, and 60 degrees.

6. The apparatus of claim 1 wherein at least one of the two or more predetermined view directions are selected either manually by a user or automatically by the computer.

7. The apparatus of claim 1 wherein projection angles of the tomosynthesis image dataset closer to the at least one of the two or more predetermined view directions are more densely sampled than projection angles farther away from the at least one of the two or more predetermined view directions.

8. The apparatus of claim 1 wherein at least one of an x-ray dose-per-projection is lower, an image resolution is lower, and an x-ray source speed is higher at projection angles of the tomosynthesis image dataset closer to the at least one of the two or more predetermined view directions than at projection angles farther away from the at least one of the two or more predetermined view directions.

9. The apparatus of claim 1 wherein the apparatus further comprises a curved holder for immobilizing the object.

10. The apparatus of claim 1 wherein slice positions in each of the two or more 3D volumes are oriented to be substantially orthogonal to the respective predetermined view directions and non-parallel with respect to the detector.

11. The apparatus of claim 10 wherein the computer is further programmed to display at least one image corresponding to at least one of the two or more 3D volumes, and wherein a point location in a first 3D volume is displayed and highlighted based on a selection of a corresponding point location in a second 3D volume.

12. The apparatus of claim 1 wherein slice positions in each of the two or more 3D volumes are oriented relative to a common 3D coordinate system.

13. The apparatus of claim 12 wherein the computer is further programmed to display at least one image corresponding to two or more 3D volumes, wherein corresponding slices in at least two of the two or more 3D volumes are displayed simultaneously.

14. The apparatus of claim 1 wherein the two or more 3D volumes are adapted to correspond to the two or more predetermined view directions by post-filtering using a single reconstructed 3D dataset.

15. A method of forming three-dimensional images of an object, the method comprising:
irradiating the object with a beam of x-rays at a plurality of positions along a path during a single scan, wherein the beam of x-rays is emitted from an x-ray source;
acquiring a tomosynthesis image dataset based on x-rays detected by an x-ray detector during the single scan; and
reconstructing two or more three-dimensional (3D) volumes from the tomosynthesis image dataset, wherein the reconstructing of the two or more 3D volumes is adapted to two or more predetermined view directions, and wherein at least one of the two or more predetermined view directions is aligned outside of a central view direction, the at least one predetermined view direction corresponding to a location of the x-ray source different than a location of the x-ray source corresponding to the central view the at least one predetermined view direction being non-orthogonal to an x-ray detector plane of the x-ray detector and distinct from a view direction of the central view.

16. The method of claim 15 further comprising optimizing the reconstruction of the two or more 3D volumes based on an orientation of the two or more predetermined view directions.

17. The method of claim 15 further comprising adjusting imaging parameters based on an orientation of the two or more predetermined view directions, wherein the imaging parameters comprise at least one of projection angles, dose-per-angle, x-ray source speed during acquisition, image resolution, and field-of-view.

18. The method of claim 15 wherein the reconstruction of the two or more 3D volumes uses one of filtered backprojection (FBP), generalized filtered backprojection (GFPB), maximum likelihood (ML-EM), algebraic reconstruction technique (ART), direct algebraic reconstruction technique (DART), and matrix inversion tomosynthesis (MITS).

19. The method of claim 15 wherein the reconstruction of at least one of the two or more 3D volumes is based on a subset of the tomosynthesis image dataset corresponding to projection angles proximate to the at least one of the two or more predetermined view directions, and wherein another subset of the tomosynthesis image dataset corresponding to projection angles farther from the at least one of the two or more predetermined view directions are discarded.

20. The method of claim 15 further comprising viewing the reconstructed two or more 3D volumes, wherein the two or more 3D volumes are viewed in one of a slice-by-slice mode or as a volume rendering.

21. A tomosynthesis Imaging system for forming three-dimensional images of an object, the system comprising:
an x-ray source configured to irradiate the object with x-rays;
an x-ray detector positioned relative to the x-ray source to detect x-rays transmitted by the x-ray source; and
a computer programmed to:
translate one of the x-ray source and the x-ray detector during a single scan such that one of the x-ray source and the x-ray detector travels along a path with respect to an object to be imaged during the single scan;
acquire a tomosynthesis image dataset; and
reconstruct two or more three-dimensional (3D) volumes from the tomosynthesis image dataset, wherein the two or more 3D volumes correspond to two or more predetermined view directions, respectively, and wherein at least one of the two or more predetermined view directions is oriented outside of a central view direction, the at least one predetermined view direction corresponding to a location of the x-ray source different than a location of the x-ray source corresponding to the central view, the at least one predetermined view direction being non-orthogonal to an x-ray detector plane of the x-ray detector and distinct from a view direction of the central view.

22. The system of claim 21 wherein the computer is further programmed to alter imaging parameters based on an orientation of at least one of the two or more predetermined view directions.

23. The system of claim 22 wherein the imaging parameters comprise at least one of projection angles, dose-per-angle, x-ray source speed during acquisition, image resolution, and field-of-view.

24. The system of claim 21 further comprising at least one curved object support, wherein the at least one curved object support is configured to support the object to be imaged.

* * * * *